United States Patent [19]

Benkmann

[11] Patent Number: 4,498,910
[45] Date of Patent: Feb. 12, 1985

[54] SAFE ADSORPTION PROCESS FOR THE SEPARATION OF HYDROCARBONS FROM OXYGEN CONTAINING GAS

[75] Inventor: Christian Benkmann, Gräfelfing, Fed. Rep. of Germany

[73] Assignees: Linde Aktiengesellschaft, Wiesbaden; Chemische Werke Huels Aktiengesellschaft, Marl, both of Fed. Rep. of Germany

[21] Appl. No.: 450,596

[22] Filed: Dec. 17, 1982

[30] Foreign Application Priority Data

Dec. 18, 1981 [DE] Fed. Rep. of Germany ....... 3150137

[51] Int. Cl.³ .............................................. B01D 53/04
[52] U.S. Cl. .......................................... 55/18; 55/26; 55/62; 55/68; 585/821; 585/826
[58] Field of Search ................... 55/25, 26, 58, 62, 74, 55/75, 18; 585/821, 826–829

[56] References Cited

U.S. PATENT DOCUMENTS

| 3,142,547 | 7/1964 | Marsh et al. | 55/26 |
| 3,176,444 | 4/1965 | Kiyonaga | 55/26 |
| 3,176,445 | 4/1965 | Collins et al. | 55/58 |
| 3,338,030 | 8/1967 | Feldbauer, Jr. | 55/25 |
| 3,430,418 | 3/1969 | Wagner | 55/25 |
| 3,564,816 | 2/1971 | Batta | 55/26 |
| 3,636,679 | 1/1972 | Batta | 55/26 |
| 4,025,321 | 5/1977 | Anderson et al. | 55/62 X |
| 4,259,091 | 3/1981 | Benkmann | 55/25 |
| 4,280,824 | 7/1981 | Lassmann et al. | 55/26 |
| 4,299,596 | 11/1981 | Benkmann | 55/26 |
| 4,305,734 | 12/1981 | McGill | 55/62 X |
| 4,371,380 | 2/1983 | Benkmann | 55/26 |

FOREIGN PATENT DOCUMENTS 2840357 4/1980 Fed. Rep. of Germany .......... 55/26
2916585 11/1980 Fed. Rep. of Germany .......... 55/26

Primary Examiner—Robert Spitzer
Attorney, Agent, or Firm—Millen & White

[57] ABSTRACT

In a pressure swing adsorption process conducted in a plurality of cyclically interchangeable adsorbers, for recovering a hydrocarbon, e.g., ethylene, from a gaseous feed stream containing hydrocarbons and less than 15% by volume of oxygen, the steps of:

(a) selectively adsorbing the hydrocarbon to be recovered during an adsorption phase conducted under elevated pressure;

(b) during the adsorption phase and during at least one cocurrent expansion phase following the adsorption phase, withdrawing a gaseous stream, at the outlet end of an adsorber, which stream is depleted in the hydrocarbon to be recovered;

(c) during a subsequent countercurrent expansion phase of desorption, withdrawing a stream enriched in the desorbed hydrocarbon to be recovered from the inlet end of the adsorber; and (d) after the desorption in step (c), conducting a pressure buildup phase by repressurizing the adsorber to the adsorption pressure with a gas containing less than 15% by volume oxygen, preferably the feed gas; and as required, withdrawing gas before the repressurizing is completed so as to prevent localized increased concentrations of oxygen, and then repeating the cycle.

21 Claims, 2 Drawing Figures

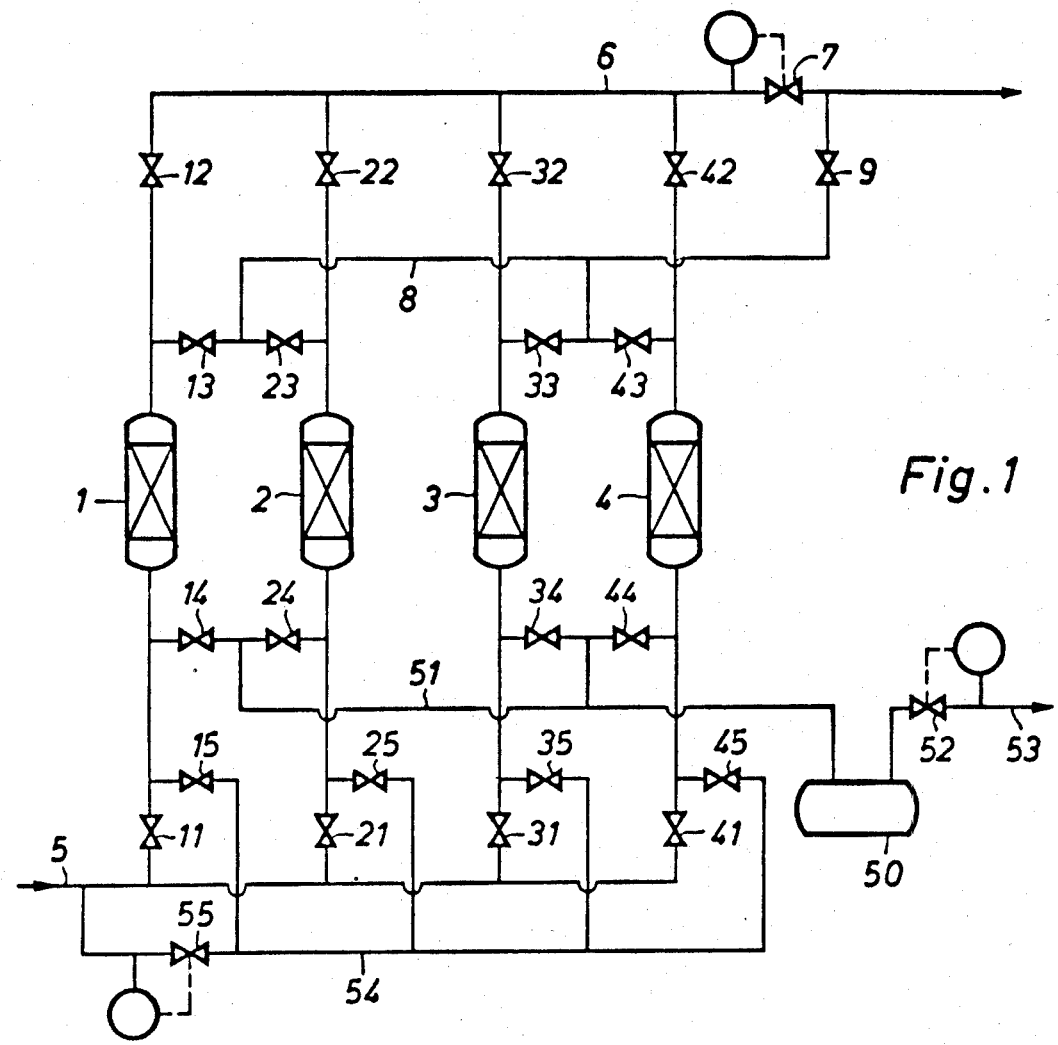

SAFE ADSORPTION PROCESS FOR THE SEPARATION OF HYDROCARBONS FROM OXYGEN CONTAINING GAS

BACKGROUND OF THE INVENTION

This invention relates to a pressure swing adsorption process for obtaining a hydrocarbon from a gaseous stream containing hydrocarbons and a small amount of oxygen.

DOS No. 3,035,255 discloses a process for obtaining or recovering hydrocarbons from a gaseous stream containing hydrocarbons and a carrier gas, wherein methane in particular is separated in a pressure swing adsorption installation from a methane-air mixture. In this system, essentially methane-free air is discharged from the outlet end of the adsorbers while enriched methane is obtained as a stream of desorbate during the regenerating phase of the adsorbers. This method is oriented toward the complete separation of all hydrocarbons, especially toward the complete separation of methane from a methane-air mixture. The adsorption process proposed for this purpose contains, as an essential process step, an air displacement step with readily adsorbable components, especially with the methane to be obtained as the product, subsequently to an adsorption phase. Such a displacement step, effected to adsorption pressure, i.e. the highest process pressure, is disadvantageous because recompression of the methane to adsorption pressure is required for this purpose.

The hydrocarbon concentration in the applications contemplated by DOS No. 3,035,255 is relatively low; methane concentrations are cited of between 1 and 40 vol-% in the raw gas. Since the additional component is to be air, oxygen concentrations of about 12-20 vol-% are encountered in the raw gas. With such a high oxygen content, however, there is very great danger of explosion of the mixture so that operation of such a plant appears to be hazardous.

Also when processing raw gases of a low oxygen content, there is the danger that localized oxygen concentrations may occur in the adsorption plant shifting the hydrocarbonoxygen mixture into the explosive range.

SUMMARY

An object of the present invention is to provide a process of the aforementioned type wherein individual hydrocarbons can be safely removed from a hydrocarbon mixture contaminated by small amounts of oxygen, e.g., not more than about 5% by volume of oxygen, generally in the range of 1 to 10%.

Upon further study of the specification and appended claims, further objects and advantages of this invention will become apparent to those skilled in the art.

The process of this invention comprises the steps of: selectively adsorbing the hydrocarbon to be obtained during an adsorption phase under elevated pressure; during the adsorption phase and during at least one cocurrent expansion phase following the adsorption phase, withdrawing from the outlet end of an adsorber a stream depleted in the hydrocarbon to be obtained; withdrawing from the inlet end of the adsorber during a subsequent countercurrent expansion, a stream of desorbate (desorbed product) enriched in the hydrocarbon to be obtained; and after desorption, repressurizing the adsorber to the adsorption pressure with a gas low in oxygen.

In the process of this invention, various streams of gaseous mixtures are encountered; and in all such streams the oxygen content of these mixtures is kept so low that there is no danger of explosion. The limitation of the oxygen concentration required for this purpose depends, in an individual case, on the respective gas composition as well as on the process conditions under which the gas is produced and processed. For example, the explosive limit for gases having a predominant proportion of methane and ethylene lies, with a pressure of 10 bar, at an oxygen concentration of about 19%, while such limit, with a pressure of 20 bar, is an oxygen concentration of about 16%. In general, for a safe operation, the oxygen content should be maintained below 15%, preferably below 12%, in particular below 10%. In any case, the concentration of oxygen should be not more than 90%, especially not more than 80%, of the explosive limit calculated for every stream.

During a pressure swing adsorption process, individual components are retained in the adsorbers, so that there results a local as well as chronological variation in the gas composition. In this connection, care must be taken, to ensure safe operation of the process, that the maximally permissible oxygen concentration is not exceeded at any time and at any location.

For conducting the pressure swing adsorption, heretofore, processes proved to be especially advantageous wherein, for pressurizing a regenerated adsorber, there was used, at least partially, gas withdrawn during an expansion phase from the adsorber, following the adsorption phase. This is usually an expansion gas withdrawn from the adsorber cocurrently with the adsorption direction, the composition of this expansion gas corresponding substantially to the composition of the unadsorbed gaseous stream withdrawn during the adsorption. Such a mode of operating the process utilizes in an energy efficient manner the pressure of the expansion gases and moreover leads to an increased yield of the component to be obtained, such component being usually the unadsorbed process stream. Processes of this type are disclosed, for example, in German Pat. No. 1,769,936; DOS No. 2,840,357; or DOS No. 2,916,585.

It has now been found that it is impossible in many cases to apply these actually well-proved methods to the separation of individual hydrocarbons from hydrocarbon mixtures containing oxygen, because unduly high oxygen concentrations are encountered in this procedure. Consequently, in the process of this invention, at least one hydrocarbon is selectively adsorbed, while other hydrocarbons, oxygen, and any further components, which may be contained in the gas, flow through the adsorber and exit in an enriched state from the adsorber. During a cocurrent expansion following the adsorption phase, a gas with a comparable composition likewise exits from the adsorber. An oxygen content which lies below the explosive limit must also still be maintained in these enriched gases wherein the entire oxygen content of the raw gas is recovered. Moreover, the essential aspect of the invention is that this gas, even then, must not be employed for the pressure buildup of a regenerated adsorber. For it was discovered that a local oxygen concentration is built up when introducing this gas into an adsorber to be repressurized, which concentration leads easily to exceeding the maximally permissible oxygen concentration. This occurs because uniform oxygen distribution does not take place in the adsorber to be pressurized; rather, there is an oxygen concentration which increases in the direction toward the outlet end of the adsorber.

For this reason, the pressure buildup of a regenerated adsorber is carried out with a gas low in oxygen in the process of this invention. Suitable as such a gaseous stream is in many cases the gaseous stream to be separated, the oxygen content of which is lower than that of the gas exiting from the adsorber end. Optionally, pressurizing can, however, also be effected with other suitable and available gaseous streams, for example methane. The use of foreign gases free of oxygen, such as methane, is advantageous, in particular, if a relatively high oxygen concentration prevails initially in the gaseous stream.

A nonuniform distribution of the oxygen concentration is also produced in the adsorber if the adsorbers are pressurized with a gas of low oxygen content, as represented by the gaseous mixture to be separated. From the raw gas utilized for pressurizing, the hydrocarbons to be obtained are selectively separated with the formation of an adsorption front moving toward the outlet end, while the unadsorbed components can immediately advance up to the closed outlet end of the adsorber. However, by the retention of individual components, there is thus a rise in oxygen concentration toward the outlet end of the adsorber. The increase in oxygen concentration depends, inter alia, also on the selectivity of the adsorbent for the hydrocarbon to be obtained. Thus, for example, when separating a gaseous stream containing predominantly methane and ethylene, and with the use of activated carbon as the adsorbent, the coadsorption of methane, besides the desired adsorption of ethylene, is relatively extensive, whereby a higher oxygen concentration occurs at the outlet end of the adsorber than, for example, with the use of silica gel as the adsorbent.

In a further development of the process of this invention, for avoiding undesirably or dangerously high oxygen concentrations at the outlet end of the adsorber during a pressurizing phase, the gas is withdrawn via the outlet end of the adsorber before termination of the pressure buildup phase.

This can be effected by control means generally known in the art, for example by a flow controller.

By means of the above described step, dangerous oxygen peak concentrations are prevented from forming. When obtaining ethylene from gaseous streams containing methane and ethylene, this mode of operation is especially expedient if activated carbon is utilized as the adsorbent. When using silica gel as the adsorbent, this version of the process, effected for safety reasons, becomes unnecessary.

Following an adsorption phase, a cocurrent expansion is conducted in the process of this invention, during which a cocurrent expansion gas is discharged essentially devoid of the component to be adsorbed, which gas escapes from the voids in the adsorbent packing during cocurrent expansion. The adsorption phase is interrupted at a point in time when the adsorption front has not as yet reached the outlet end of the adsorber so that, during the cocurrent expansion phase, the components to be obtained, still contained in the gaseous mixture filling the voids, are separated while the adsorption front advances further toward the outlet end of the adsorber.

Although the gaseous mixture obtained during the cocurrent expansion phase and exhibiting an oxygen content higher than that of the raw gas must not be utilized for pressurizing a regenerated adsorber, such mixture can be utilized, due to its low concentration of the component to be obtained, for scavenging an adsorber prior to the pressurizing phase. Such a scavenging step can follow the countercurrent expansion of the adsorber, during which the actual product fraction is withdrawn, so that optionally a residual load on the adsorber is reduced. However, scavenging of the adsorber is not required in each and every case.

The stream of desorbate produced during countercurrent expansion contains the hydrocarbon to be obtained in a concentration depending on the concentration in the raw gas as well as on the selectivity of the adsorbent. If the concentration of the desired product component in this gaseous stream is still inadequate, then this stream of desorbate can be separated, in a further separator, into a highly enriched stream of the hydrocarbon to be obtained and into a residual gas stream. Suitable for such a subsequent separation is, for example, another pressure swing adsorption installation.

It is possible in some cases for the raw gas stream to be separated to contain components more readily adsorbable than the hydrocarbon to be recovered. In such a case, in a further embodiment of the process of this invention, the more readily adsorbable components are separated in adsorbers installed upstream, optionally using a different adsorbent. Such upstream adsorbers can be arranged in a separate adsorber station or also can be designed as preliminary beds in connection with the actual adsorber beds and can be arranged in a common housing together with the primary adsorbers. An especially suitable scavenging gas for regenerating such upstream adsorbers is the gaseous stream exiting from the outlet end of the primary adsorbers. This mode of operation is advantageous, in particular, if the unadsorbed gas is obtained as a low-quality residual gas which can be used only for heating purposes, for example.

Adsorption installations having at least three adsorbers, preferably at least four adsorbers, are particularly suitable for the process of this invention.

BRIEF DESCRIPTION OF DRAWINGS

Additional details of the invention will be described below with reference to a preferred comprehensive embodiment schematically illustrated in the figures.

In the drawings:
FIG. 1 is an installation for conducting the process of this invention; and
FIG. 2 is a time schedule flow chart for the operation of the plant according to FIG. 1.

DETAILED DESCRIPTION

The pressure swing adsorption installation shown in FIG. 1 comprises four adsorbers 1, 2, 3, and 4. The adsorbers are connected on the inlet side via valves 11, 21, 31 and 41 to a raw gas conduit 5 and on the outlet side via vanes 12, 22, 32, and 42 to a residual gas conduit 6 through which the unadsorbed components of the raw gas are withdrawn. Prior to discharge of the residual gas, the pressure is reduced in the controllable expansion valve 7. Furthermore, the outlet ends of the adsorbers are connected via the valves 13, 23, 33 and 43, respectively, to a conduit 8 in communication with the residual gas conduit via the valve 9. Expansion gases produced during a first expansion phase and rich in unadsorbed components are discharged into the residual gas by way of this conduit.

Valves 14, 24, 34 and 44, respectively, are provided on the inlet side of the adsorbers, connecting the inlet end of the adsorbers with a conduit 51 leading to the buffer or surge tank 50. Tank 50 is connected to the product conduit 53 by way of a control valve 52. The product gas obtained during a countercurrent expansion, as well as scavenging gas and desorbate produced during a scavenging phase are introduced into tank 50 by way of conduit 51.

Finally, valves 15, 25, 35, and 45 are arranged on the inlet side of the adsorbers, these valves being connected via conduit 54 and control valve 55 with the raw gas conduit 5. The pressure buildup of the scavenged adsorbers by means of raw gas is effected via this conduit.

FIG. 2 illustrates the time schedule for the operation of the installation. The four adsorbers pass through identical cycles chronologically displaced with respect to one another so that one adsorber is always in the adsorption phase, thus ensuring continuous operation. The adsorption phase ADS, conducted under constant pressure, is followed by a first expansion E1 in cocurrent mode. The thus-formed expansion gas is discharged into the residual gas. In a second cocurrent expansion phase E2, further gas is withdrawn via the outlet end of the adsorber. This gas passes via the opened valves 13 and 43 to the outlet end of the adsorber 4 and flows through the adsorber 4, which is in a scavenging phase S, before it is conducted via valve 44 and conduit 51 into the buffer tank 50. Following the second cocurrent expansion, a countercurrent expansion phase E3 is conducted, during which a stream of desorbate is conducted via the opened valve 14 and conduit 51 to the buffer tank 50. After termination of the counter-current expansion E3 the adsorber is subjected to a scavenging phase S. For this purpose, expansion gas from the cocurrent expansion phase E2 of the adsorber 2 is conducted via the opened valves 23 and 13 countercurrently to the adsorption direction through the adsorber 1. The scavenging gas effects displacement of the adsorbed product component, which latter exits, in a still high concentration, from the inlet end of the adsorber. The scavenging phase is kept relatively short to avoid unnecessary dilution of the product gas conducted to the buffer tank 50 with scavenging gas. In another version of the process, it is also possible to conduct, instead of the scavenging step S, a desorption with the use of subatmospheric pressure. The thus-attained improvement in product quality, however, is achieved at the cost of increased energy expenditure for a vacuum pump.

After completion of the scavenging phase S, the adsorber can be repressurized to the adsorption pressure. This is done during the pressure buildup phase B, during which raw gas is conducted into the adsorber 1 via the opened valves 55 and 15. After the raw gas pressure has been build up in adsorber 1, the latter has completed a whole cycle. The remaining adsorbers pass through the same cycle but on a displaced time schedule, as illustrated in FIG. 2.

The process of this invention is especially suitable, for example, for the separation of waste gases from plants for ethylene oxide production; these waste gases can contain essentially valuable ethylene, less valuable methane, small amounts of oxygen, as well as in some cases additionally inert gases, such as argon, nitrogen, or carbon dioxide, and other lighter hydrocarbons. The amount of ethylene contained in such a gaseous stream depends on the method used for the production of ethylene oxide and is typically in the range of 10–40%, e.g., about 25 mol-%, while the oxygen content ranges generally between about 1 and 7 mol-%, especially, in case ethylene oxide is produced with oxygen, in a range of about 5–7 mol-%.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever. In the following example, all temperatures are set forth uncorrected in degrees Celsius; unless otherwise indicated, all parts and percentages are by volume.

Ethylene is converted in an ethylene oxide plant with oxygen to produce ethylene oxide. A purge gas is withdrawn from the plant in an amount of 500 Nm³/h at a pressure of 10 bar and a temperature of 40° C. This gas has the following composition:

| | |
|---|---|
| Methane | 50% |
| Ethylene | 28% |
| Ethane | 1% |
| Oxygen | 5% |
| Carbon Dioxide | 6% |
| Inert Gases | 10%. |

For recovering the ethylene content of this gas, it is conducted to an adsorption plant as described with reference to the drawing. Silicagel is used as adsorbent and the plant operates with a cycle time of 16 minutes, the duration of each adsorption phase being 4 minutes. From the outlet end of the adsorption plant, a residual gas with reduced ethylene content is withdrawn in an amount of 222 Nm³/h at a pressure of 6 bar and at a temperature of 40° C.

The composition of the residual gas is as follows:

| | |
|---|---|
| Methane | 69.9% |
| Ethylene | 1.7% |
| Ethane | 1.4% |
| Oxygen | 9.0% |
| Inert Gases | 18.0%. |

During the regeneration of previously loaded adsorbers an ethylene rich gas is obtained in an amount of 278 Nm³/h at a pressure of 1.5 bar and a temperature of 40° C. The composition of this gas is as follows:

| | |
|---|---|
| Methane | 34.1% |
| Ethylene | 49.0% |
| Ethane | 0.7% |
| Oxygen | 1.8% |
| Carbon Dioxide | 10.8% |
| Inert Gases | 3.6%. |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

I claim:

1. A pressure swing adsorption process conducted in a plurality of cyclically interchangeable adsorbers, for recovering a hydrocarbon from a gaseous feed stream containing hydrocarbons and a minor amount of oxygen, comprising the steps in a cycle of:
    (a) selectively adsorbing the hydrocarbon to be recovered during an adsorption phase conducted under elevated pressure;
    (b) during the adsorption phase and during at least one cocurrent expansion phase following the adsorption phase, withdrawing a residual gaseous stream, at the outlet end of an adsorber, which stream is depleted in the hydrocarbon to be recovered and enriched in oxygen;
    (c) during a subsequent countercurrent expansion phase of desorption, withdrawing a stream enriched in the desorbed hydrocarbon to be recovered from the inlet end of the adsorber; and
    (d) after the desorption in step (c), conducting a pressure buildup phase by repressurizing the adsorber to the adsorption pressure with the gaseous feedstream or a gas free of oxygen so as to prevent the occurrence of localized concentrations of oxygen within the adsorber of above 90% of the explosive limits thereof, and then repeating the cycle.

2. A process according to claim 1, wherein the gas used for repressurizing is the gaseous feed stream to be separated.

3. A process according to claim 2, further comprising withdrawing a portion of the gaseous stream depleted in the hydrocarbon to be recovered via the outlet end of the adsorber before completion of the pressure buildup phase.

4. A process according to claim 1, further comprising withdrawing a portion of the gaseous stream depleted in the hydrocarbon to be recovered via the outlet end of the adsorber during the pressure buildup phase but before completion thereof.

5. A process according to claim 4, further comprising an upstream step in a preliminary adsorber of selectively adsorbing components contained in the gaseous feed stream which are more readily adsorbable than the hydrocarbon to be recovered; and employing the gas in step (b) exiting at the outlet end of the adsorber and depleted in the hydrocarbon to be recovered to purge the preliminary adsorber so as to regenerate same.

6. A process according to claim 1, further comprising feeding the hydrocarbon-enriched stream of step (c) to a further pressure swing adsorption process to separate said enriched stream into a more highly enriched stream of the hydrocarbon to be recovered and into a residual gas stream.

7. A process according to claim 1, further comprising an upstream step in a preliminary adsorber of selectively adsorbing components contained in the gaseous feed stream which are more readily adsorbable than the hydrocarbon to be recovered; and employing the gas in step (b) exiting at the outlet end of the adsorber and depleted in the hydrocarbon to be recovered to purge the preliminary adsorber so as to regenerate same.

8. A process according to claim 1, wherein the gaseous feed stream contains primarily methane and ethylene as the hydrocarbons, and ethylene is the hydrocarbon to be recovered.

9. A process according to claim 8, wherein silica gel or activated carbon is used as the adsorbent.

10. A process according to claim 8, wherein activated carbon is used as the adsorbent.

11. A process according to claim 10, further comprising withdrawing a portion of the gaseous stream depleted in the hydrocarbon to be recovered via the outlet end of the adsorber before completion of the pressure buildup phase.

12. A process according to claim 1, wherein the minor amount of oxygen in the feedstream constitutes 1-10% by volume.

13. A process according to claim 12, wherein the minor amount of oxygen in the feedstream constitutes not more than 5% by volume.

14. A process according to claim 1, wherein the gas used for repressurizing is a gas free of oxygen.

15. A process according to claim 1, wherein the gas used for repressurizing is methane.

16. A process according to claim 15, wherein the hydrocarbon to be recovered is ethylene.

17. A process according to claim 1, wherein the gaseous feedstream is a waste gas from ethylene oxide production.

18. A process according to claim 1, wherein the hydrocarbon to be recovered in ethylene.

19. A process according to claim 1, wherein the process is controlled so that the concentration of oxygen is not more than 90% of the explosive limit calculated for every stream.

20. A process according to claim 19, wherein the concentration of oxygen is not more than 80% of the explosive limit.

21. A pressure swing adsorption process conducted in a plurality of cyclically interchangeable adsorbers, for recovering a hydrocarbon from a gaseous feed stream containing hydrocarbons and a minor amount of oxygen, comprising the steps in a cycle of:
    (a) selectively adsorbing the hydrocarbon to be recovered during an adsorption phase conducted under elevated pressure;
    (b) during the adsorption phase and during at least one cocurrent expansion phase following the adsorption phase, withdrawing a residual gaseous stream from an adsorber, which stream is depleted in the hydrocarbon to be recovered and enriched in oxygen;
    (c) during a subsequent countercurrent expansion phase of desorption, withdrawing a stream enriched in the desorbed hydrocarbon to be recovered from the adsorber; and
    (d) after the desorption in step (c), conducting a pressure buildup phase by repressurizing the adsorber to the adsorption pressure with the gaseous feedstream or a gas free of oxygen so as to prevent the occurrence of localized concentrations of oxygen within the adsorber of above 90% of the explosive limits thereof, and then repeating the cycle.

* * * * *